United States Patent [19]

Starks

[11] 3,932,552
[45] Jan. 13, 1976

[54] INTEGRATED PROCESS FOR PRODUCING $C_2$ HYDROCARBONS FROM CARBON MONOXIDE AND HYDROGEN

[75] Inventor: Charles M. Starks, Ponca City, Okla.

[73] Assignee: Continental Oil Company, Ponca City, Okla.

[22] Filed: Mar. 25, 1974

[21] Appl. No.: 454,488

[52] U.S. Cl............... 260/682; 260/450; 260/683 R
[51] Int. Cl.² ......................................... C07C 3/40
[58] Field of Search................ 260/450, 682, 683 R

[56] References Cited
UNITED STATES PATENTS

| | | | |
|---|---|---|---|
| 2,600,452 | 6/1952 | Voorhies | 260/682 |
| 2,623,074 | 12/1952 | Ratcliff | 260/682 |
| 2,948,745 | 8/1960 | Riordan et al. | 260/450 |
| 3,842,138 | 10/1974 | Chahvekilian et al. | 260/683 R |

*Primary Examiner*—Paul M. Coughlan, Jr.
*Attorney, Agent, or Firm*—Cortlan R. Schupbach, Jr.

[57] ABSTRACT

$C_2$ hydrocarbons may be produced from carbon monoxide and hydrogen using an integrated process scheme involving reacting carbon monoxide and hydrogen to produce a hydrocarbon effluent containing hydrogen and subsequently hydropyrolyzing said effluent and recovering $C_2$ hydrocarbons.

11 Claims, No Drawings

INTEGRATED PROCESS FOR PRODUCING C₂ HYDROCARBONS FROM CARBON MONOXIDE AND HYDROGEN

This invention relates to an integrated process for producing ethane and/or ethylene from carbon monoxide and hydrogen.

In general, ethane and ethylene are regarded as most valuable materials, being among the cornerstones of the synthetic chemical industry. Heretofore, ethane has been commercially obtained from natural gas and distillation of crude petroleum while ethylene has been obtained principally from the pyrolysis of various petroleum fractions ranging from ethane to heavy gas oil or even whole crude. In some areas, ethylene has typically been obtained by pyrolysis of naphtha, liquid petroleum gas or kerosene. Quite obviously with the decline of available reserves of natural gas and petroleum crude, there is a need for alternative means for producing ethane and ethylene which are not dependent upon natural gas and petroleum feedstocks.

In accordance with this invention, there is provided an integrated process wherein ethane and/or ethylene is produced from carbon monoxide and hydrogen, two materials which are plentiful and not dependent on natural gas or petroleum for supply. Briefly described, the integrated process involves catalytically reacting carbon monoxide and hydrogen to form a gaseous effluent containing a mixture of hydrocarbons, oxygenated hydrocarbons, and hydrogen among other materials, feeding this gaseous effluent to a pyrolysis zone and non-catalytically hydropyrolyzing the effluent under pressure to produce a product mixture containing significant amounts of $C_2$ hydrocarbons, methane, and small amounts of higher hydrocarbons of which a predominant portion is benzene and toluene. In addition, unreacted hydrogen and carbon monoxide may be conveniently recycled as can be any higher hydrocarbons.

Beginning with the catalytic reaction of hydrogen and carbon monoxide, it is pointed out that this is basically a Fischer-Tropsch synthesis. Fischer-Tropsch syntheses have long been known in the art and are well documented in the literature. However, the details of this catalytic reaction as it applies to the integrated process of the invention are described hereinafter.

The essential components of the feedstock for the catalytic reaction are hydrogen and carbon monoxide. In general, the mol ratio of hydrogen to carbon monoxide should be at least 1/1, and preferably at least 1.5/1. Low amounts of hydrogen decrease the reaction rate and, perhaps more importantly, tend to result in some disassociation of the carbon monoxide to carbon dioxide and elemental carbon. The formation of carbon is undesirable as it deposits out on the interior of the reaction zone and on the catalyst. This results in decreased heat transfer, a factor which may be significant in view of the exothermic nature of the reaction, and in decreased activity of the catalyst. As the mol ratio of hydrogen to carbon monoxide increases the rate of reaction generally increases up to a point after which it either remains somewhat constant or even tapers off. In addition, high amounts of hydrogen generally tend to result in lower average molecular weight products with saturated compounds favored over unsaturated compounds. Another factor to be considered with high amounts of hydrogen is that the unconsumed hydrogen must be carried through and subsequently be separated in the process, even though it may be recycled. Considering all of these aspects, it is generally desired to operate the process with a mol ratio of hydrogen to carbon monoxide of less than about 5/1, and preferably in the range of about 2/1 to 4/1.

A portion of the hydrogen and carbon monoxide to the reaction may be provided by introducing water (steam) and carbon dioxide as part of the feedstock. Under conditions of the reaction, the well-known water gas shift takes place to some extent as follows:

$$H_2O + CO \rightleftharpoons H_2 + CO_2$$

However, the reversible nature of the reaction should be taken into consideration in determining the amounts of water or carbon monoxide to be included in the feedstock.

It is further mentioned that the hydrogen carbon monoxide feedstock can contain other materials such as methane or higher hydrocarbons or oxygenated hydrocarbons or inert materials such as nitrogen, argon, and the like. In fact, for reactor control, it may be desirable to recycle a portion of the effluent or part of the effluent from the catalytic reaction zone after being cooled. When other materials are present, it is generally desirable to maintain the hydrogen carbon monoxide concentration as high as possible consistent with maintaining control over the reaction zone.

Sulfur compounds such as $H_2S$ or COS in the feedstock are undesirable as they tend to deactiviate the catalyst. Thus, if the feedstock contains more than tolerable traces of such sulfur compounds, it may become necessary to replace the catalyst more often than would normally be acceptable.

A particularly suitable source of a feedstock for the catalytic reaction is the effluent from gasification of coal with steam and oxygen which has been suitably treated to remove sulfur compounds as known in the art. Such effluents contain considerable quantities of hydrogen and carbon monoxide along with some methane, carbon dioxide, water and possibly higher hydrocarbons. If the mol ratio of hydrocarbon to carbon monoxide is lower than that desired, the effluent may be subjected to a water gas shift reaction to increase the ratio to the desired value. It may also be adjusted from external sources of hydrogen. While not necessarily essential, the gasification effluent may also be subjected to a separation step; e.g., cryogenic separation, to remove most of the carbon dioxide, water, methane, and higher hydrocarbons to provide a feedstock consisting essentially of only hydrogen and carbon monoxide.

The catalytic reaction may be conducted at temperatures in the range of about 150°C to about 450°C. Lower temperatures tend to result in higher molecular weight products which may cause fouling of the catalyst or reaction zone. On the other hand, higher temperatures tend to result in production of carbon which likewise may cause catalyst fouling. Preferred temperatures are in the range of 200°C to 400°C with the most preferred temperatures ranging from 250°C to 350°C.

Pressures as low as atmospheric pressure may be employed but the reaction rate is relatively slow at low pressures. Higher pressures may also be used with the primary considerations being equipment design, possible reactor and catalyst fouling due to the fact that higher pressures tend to result in higher molecular weight products, and reaction control since increased pressure increases the reaction rate. Generally, pressures in the range of 5 to 75 atmospheres gauge will be used, preferably 10 to 30 atmospheres gauge.

The catalytic reaction may be conducted in a zone containing a conventional fixed or fluidized (fixed or entrained types) catalyst bed. Normally the fluidized bed is employed. Space velocities in the range of about 500 too 50,000 volumes of feedstock/volume of catalyst/hour at standard temperature and pressure conditions may be used, preferably in the range of 3,000 to 10,000 V/V/hr STP.

The catalysts useful for the catalytic reaction include any Fischer-Tropsch catalyst containing iron, cobalt, nickel or ruthenium. These catalysts are well known in the art being described in the Fischer-Tropsch and Related Syntheses by Storch et al, John Wiley and Sons, 1951, Chapter 3, all of which is incorporated herein by reference. As also well known in the art and described in the referenced text, these catalysts may be supported and may be promoted or activated by numerous materials. All of this is intended to be encompassed by the phrase "Fischer-Tropsch catalyst" as used herein. Further examples of suitable Fischer-Tropsch catalysts appear in U.S. Pat. Nos. 2,543,327 and 2,944,988, also incorporated herein by reference.

A particularly preferred Fischer-Tropsch catalyst is one containing iron and promoted or activated with alumina, magnesium oxide, calcium oxide, potassium oxide, silica, manganese oxide, thoria, titania, molybdenum oxide, or mixtures thereof. Suitable sources of iron component include mill scale and magnetite with the latter already containing some of promoters or activators.

The catalytic reaction is carried out under conditions within the ranges described above to a conversion of carbon monoxide in the feedstock of at least 50 percent and wherein the effluent product system contains in the range of about 8 volume percent to 75 volume percent methane based on the total content of hydrocarbons and oxygenated hydrocarbons produced from CO. In other words, the effluent contains 25 volume percent to 92 volume percent of the total hydrocarbons and oxygenated hydrocarbons which is available for conversion to $C_2$ hydrocarbons. There is little aromatic content in these higher hydrocarbons and oxygenated hydrocarbons. There is little or no incentive to produce an effluent containing below 8 volume percent methane due to severe catalyst fouling. Preferably, the effluent product stream contains 10 volume percent to 50 volume percent, more preferably 10 volume percent to 25 volume percent, methane based on the total content of hydrocarbons and oxygenated hydrocarbons produced from CO.

In addition to the hydrocarbons and oxygenated hydrocarbons, the effluent includes carbon monoxide, hydrogen, carbon dioxide and water. The hydrogen present in the effluent is considerable, usually in excess of 1 mol of hydrogen per mol of hydrocarbons and oxygenated hydrocarbons having three or more carbon atoms ($C_3+$ hydrocarbons). This feature is of significance since the effluent is thereby particularly suitable for direct introduction as is to the hydropyrolysis step of the integrated process without additional hydrogen from an outside source.

The effluent from the catalytic reaction is then introduced to a hydropyrolysis zone, preferably without cooling. The hydropyrolysis zone is a heated zone through which the effluent passes while the $C_3+$ hydrocarbons and oxygenated hydrocarbons are pyrolytically cracked in the presence of hydrogen to $C_1$ and $C_2$ hydrocarbons. In general, it has been found that the above described catalytic reaction effluent already containing significant quantities of hydrogen is ideally suited for pyrolytic cracking of the $C_3+$ hydrocarbons and oxygenated hydrocarbons to products having a relatively high mol ratio of $C_2$ hydrocarbons to $C_1$ hydrocarbon; e.g., a 0.8/1 mol ratio or higher.

From an equipment standpoint, a suitable reactor for conducting the hydropyrolysis is described in U.S. Pat. No. 3,363,024. In addition, it is possible to employ conventional tubular furnaces of the type used in cracking petroleum derived feedstocks to ethylene.

The hydropyrolysis step is conducted with a mol ratio of hydrogen to $C_3+$ hydrocarbons and oxygenated hydrocarbons of at least 1/1, preferably in the range of about 3/1 to 30/1, most preferably 20/1. The more hydrogen present the greater the amount of ethane relative to ethylene that will be produced, in general. Quantities of hydrogen much above a 30/1 ratio do not result in any significant effects other than necessitating separation and recycle of large volumes of material.

As pointed out above, the effluent from the catalytic reaction will usually contain sufficient hydrogen to conduct the hydropyrolysis step. However, if more is desired, it may be introduced from an external source. Preferably, it is introduced to the effluent stream prior to introduction to the hydropyrolysis zone. Such external source of hydrogen advantageously consists substantially wholly of hydrogen but may contain other materials such as carbon monoxide, water, and carbon dioxide. A particularly suitable sourcee may be the product of gasifying coal with steam and oxygen or the product of a water gas switch reaction with carbon dioxide removal.

In another embodiment of the invention, the effluent from the catalytic reaction may be divided prior to introduction to the hydropyrolysis zone. One portion may be cooled and fractionated to separate the $C_3+$ hydrocarbons and oxygenated hydrocarbons from the hydrogen, carbon monoxide, carbon dioxide, water, methane, ethylene, and ethane. The latter materials, except for methane, ethane and ethylene which are recovered, may then be recycled to the feedstock for the catalytic reaction while the $C_3+$ hydrocarbons and oxygenated hydrocarbons are reintroduced back to the remaining portion of the effluent thereby increasing the concentration of hydrocarbons and oxygenated hydrocarbons of the feed to the hydropyrolysis zone.

As a further embodiment of the process, hydrocarbons from an external source may also be introduced to the catalytic reaction effluent to enrich the hydrocarbon content for hydropyrolysis. This external source may be hydrocarbons along with oxygenated hydrocarbons separated from the effluent of another catalytic reaction zone. These hydrocarbons may also be petroleum distillate streams containing predominantly paraffinic hydrocarbons.

The hydropyrolysis is carried out at temperatures in the range of 600°C to 900°C, preferably 700°C to 850°C. The higher temperatures favor ethylene over ethane. Pressures of at least 5 atmospheres gauge are employed, usually in the range of 5 to 100 atmospheres gauge and preferably in the range of 15 to 30 atmospheres gauge. The lower pressures favor ethylene over ethane. Residence times in the range of 0.1 sec to 60 sec, preferably 0.5 to 20 sec, are employed. The shorter residence times favor ethylene over ethane.

Carbon deposition in the hydropyrolysis zone can be inhibited by providing a small concentration of sulfur compounds in the feed to the zone; e.g., 10 ppm, as is known in the art. This is generally referred to as passification of the zone and is done essentially on a continuous basis throughout the operation. The use of sulfur compounds in the present process has some disadvantages in that the hydrogen, carbon monoxide, and carbon dioxide in the effluent product must be purified before recycling back to the catalytic reaction as sulfur has an adverse effect on Fischer-Tropsch catalysts.

An alternative to the use of sulfur compounds is water or stream although for a given degree of effectiveness in inhibiting carbonization greater quantities of water are required compared to sulfur compounds. Usually, up to about 3 mol of water per mol of hydrocarbon and oxygenated hydrocarbon will be effective although greater quantities can also be employed. Water not only inhibits carbonization but can be recycled in some quantities to the catalytic reaction. It further has an effect on the hydropyrolysis of tending to favor production of ethylene over ethane. Depending on the ultimate desired $C_2$ product, this effect may be used to some benefit.

The product mixture from the hydropyrolysis zone, a gas, is then processed for recovery of the $C_1$ and $C_2$ hydrocarbons by suitable techniques known in the art. A convenient recovery system involves rapidly cooling the product mixture and then processing the cooled mixture through a series of low-temperature fractional distillation columns. Hydrogen along with carbon monoxide, carbon dioxide, and water are first removed and recycled, with or without further separation, back to the catalytic reaction zone. Methane is then separated and may be utilized as a synthetic natural gas component. Ethylene and ethane are next separated and recovered. The remaining higher hydrocarbons, which include some aromatics, may be hydrogenated and recycled to the hydropyrolysis zone for reprocessing. Alternatively, aromatics such as benzene and toluene may be separated and recovered prior to hydrogenation and recycle.

While the above separation technique essentially is a selective step-wise distillation, it will be understood by those skilled in the art that a selective stepwise condensation approach may also be used.

As is apparent from the above description, the integrated process of this invention provides a unique way to produce $C_2$ hydrocarbons, ethylene, and ethane, from hydrogen and carbon monoxide, as well as other valuable by-products.

In demonstrating the integrated process of the invention, an apparatus was assembled comprising a catalytic reactor and a hydropyrolysis reactor in series. The catalytic reactor was an annularly cooled fixed fluidized-bed reactor of 1-inch diameter, N.P.S., Schedule 40, 316 stainless steel 80 inches in length equipped at the lower end with a reactant distribution plate (a porous frit disc) and at the upper end with a 3-inch diameter N.P.S. catalyst disengaging zone and a catalyst baffle and filter. The hydropyrolysis reactor was a ½ inch, 316 SS, 18 ga piece of tubing about 28 inches in length mounted within a 2-inch N.P.S. pipe furnace.

Using the above described apparatus, several runs were conducted in converting hydrogen and carbon monoxide to $C_2$ hydrocarbons. The details and results of these runs are described in the following examples.

EXAMPLE 1

A feedstock of technical grade hydrogen and carbon monoxide were separated metered along with a small amount of argon (2 percent of feedstock — used as an internal standard for GLC analysis) to a mixing zone. The hydrogen to carbon monoxide mol ratio was about 3 with the hydrogen feed rate being about 16.6 l/min STP and the carbon monoxide feed rate being about 5.54 l/min STP. After mixing, the gaseous feedstock was passed through beds of activated carbon and molecular sieves for cleanup followed by preheating to about 300°C.

The feedstock was then introduced to the catalytic reactor through the lower distribution plate. The reactor was charged with 344 g of a preconditioned Fischer-Tropsch catalyst containing iron (Armco mill scale promoted with 0.17 weight percent K in the form of $K_2O$, 0.17 weight percent Ca in the form of CaO and 3 weight percent $Al_2O_3$). The feedstock was reacted by passing it through the fixed, fluidized-bed of catalyst at a space velocity of about 5,100 hr$^{-1}$, a temperature of about 360°C and a pressure of about 17 atmospheres gauge for a conversion of CO greater than 98 percent. A sample of the effluent from the catalytic reactor was passed through a chilled water condenser and then depressurized into a collection tube. Water collected was separated and determined. The organic liquid phase and the gas phase were each analyzed by GLC. The results appear in Table I.

The effluent from the catalytic reactor, having a mol ratio of hydrogen to total hydrocarbon and oxygenated hydrocarbon having three or more carbon atoms of about 20.4, was directly introduced to the hydropyrolysis reactor wherein it was subjected to conditions of temperature of about 799°C, pressure of about 17 atmospheres and a residence time of about 0.5 second. A sample of the hydropyrolysis effluent was passed through a chilled water condenser and then depressurized into a collection tube. Water collected was separated and determined while each of the organic liquid phase and the gas phase were analyzed by GLC. The results are shown in Table I.

TABLE I

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 28.7 | 33.3 | | |
| $H_2$ | 10.1 | 7.6 | | |
| CO | 1.4 | 7.5 | | |
| $CO_2$ | 28.4 | 19.5 | | |
| $C_1$" | 12.4 | 17.2 | 39.6 | 53.6 |
| $C_2$" | 5.0 | 11.9 | 16.0 | 37.1 |
| $C_3$" | 5.3 | 2.0 | 16.9 | 6.2 |
| $C_4$" | 3.4 | 0.4 | 11.0 | 1.3 |
| $C_5$" | 2.2 | 0.1 | 7.0 | 0.2 |
| $C_6+$" | 3.0 | 0.5 | 9.6 | 1.7 |

"These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.
Note - $C_6+$ includes all materials having 6 or more carbon atoms — this same nomenclature appears in the subsequent tables.

EXAMPLE 2

Another run was performed according to the procedure described in Example 1 except that the mol ratio of hydrogen to carbon monoxide in the feedstock to the catalytic reaction was about 4, the hydrogen rate was about 13.7 l/min STP and the carbon monoxide rate was about 3.42 l/min STP.

The catalytic reaction was conducted at a temperature of about 343°C, a pressure of about 13.6 atmospheres gauge and a space velocity of about 4,200 hr$^{-1}$ to a conversion of carbon monoxide of about 98.7 percent. The effluent has a mol ratio of hydrogen to total hydrocarbons and oxygenated hydrocarbons having 3 or more carbon atoms of about 32.1.

The hydropyrolysis reaction was conducted at a temperature of about 799°C, a pressure of about 13.6 atmospheres gauge and a residence time of 0.5 second.

The analyses of the catalytic reaction effluent and the hydropyrolysis effluent are indicated in Table II.

TABLE II

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 29.3 | 33.9 | | |
| $H_2$ | 14.6 | 12.3 | | |
| CO | 1.0 | 7.1 | | |
| $CO_2$ | 24.4 | 15.5 | | |
| $C_1{}^a$ | 13.3 | 16.9 | 43.5 | 54.1 |
| $C_2{}^a$ | 5.4 | 12.3 | 17.7 | 39.6 |
| $C_3{}^a$ | 5.5 | 1.6 | 17.9 | 5.0 |
| $C_4{}^a$ | 3.3 | 0.2 | 10.7 | 0.6 |
| $C_5{}^a$ | 1.9 | 0.01 | 6.1 | 0.03 |
| $C_6+{}^a$ | 1.3 | 0.2 | 4.1 | 0.7 |

$^a$These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

EXAMPLE 3

Another run was performed according to the procedure described in Example I with the mol ratio of hydrogen to carbon monoxide in the feedstock to the catalytic reaction being about 3 except that the hydrogen rate was 13.3 l/min STP and the carbon monoxide rate was about 4.42 l/min STP and the Fischer-Tropsch iron catalyst (300 g) was formed from mill scale and contained 3 weight percent alumina and 0.13 weight percent potassium in the form of $K_2O$.

The catalytic reaction was carried out at a temperature of about 343°C, a pressure of about 13.6 atmospheres gauge and a space velocity of about 5900 hr$^{-1}$ to a conversion of carbon monoxide of about 97.6 percent. The effluent had a mole ratio of hydrogen to total hydrocarbons and oxygenated hydrocarbons having 3 or more carbon atoms of about 12.5.

The hydropyrolysis reaction was conducted at a temperature of about 799°C, a pressure of about 13.6 atmospheres gauge and a residence time of about 0.5 second.

The analyses of the catalytic reaction effluent and the hydropyrolysis effluent are set forth in Table III.

TABLE III

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 30.6 | 34.2 | | |
| $H_2$ | 8.9 | 6.8 | | |
| CO | 2.2 | 6.8 | | |
| $CO_2$ | 26.1 | 19.4 | | |
| $C_1{}^a$ | 5.2 | 11.8 | 16.1 | 36.1 |

TABLE III-continued

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $C_2{}^a$ | 3.8 | 16.2 | 11.9 | 49.4 |
| $C_3{}^a$ | 5.0 | 2.9 | 15.4 | 8.9 |
| $C_4{}^a$ | 4.3 | 0.5 | 13.4 | 1.6 |
| $C_5{}^a$ | 3.7 | 0.2 | 11.6 | 0.6 |
| $C_6+{}^a$ | 10.1 | 1.1 | 31.6 | 3.3 |

$^a$These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

EXAMPLE 4

A further run was conducted according to the procedure described in Example 1 with the mol ratio of $H_2$ to CO in the feedstock to the catalytic reaction being about 3 except that the $H_2$ rate was 19.1 l/min STP and the CO rate was 6.6 l/min STP and the Fischer-Tropsch catalyst (300 g) was the same as used in Example 3.

The catalytic reaction was carried out at a temperature of about 343°C, a pressure of about 20.4 atmospheres gauge and a space velocity of 880 hr$^{-1}$ to a conversion of CO of about 96.8 percent. The effluent had a mol ratio of hydrogen to hydrocarbons and oxygenated hydrocarbons having three or more carbon atoms of about 16.3.

The hydropyrolysis reaction was conducted at a temperature of about 807°C, a pressure of about 20.4 atmospheres gauge and a residence time of about 0.5 second. The feed to the pyrolysis reactor had a level of about 730 ppm $H_2S$ added thereto for passification of the reactor.

The analyses of the catalytic reaction effluent and the hydropyrolysis effluent are set forth in Table IV.

TABLE IV

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 29.8 | 30.6 | | |
| $H_2$ | 10.7 | 8.6 | | |
| CO | 2.6 | 2.9 | | |
| $CO_2$ | 25.6 | 25.8 | | |
| $C_1{}^a$ | 6.5 | 12.8 | 20.8 | 40.1 |
| $C_2{}^a$ | 4.5 | 15.9 | 14.5 | 49.5 |
| $C_3{}^a$ | 5.7 | 2.2 | 18.2 | 7.0 |
| $C_4{}^a$ | 4.2 | 0.4 | 13.5 | 1.1 |
| $C_5{}^a$ | 3.1 | 0.1 | 9.8 | 0.2 |
| $C_6+{}^a$ | 7.0 | 0.7 | 22.2 | 2.1 |

$^a$These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

EXAMPLE 5

Another run carried in accordance with Example 1 with the mol ratio of hydrogen to carbon monoxide in the feedstock to the catalytic reaction being about 3, except that the $H_2$ rate was 19.1 l/min STP and the CO rate was 6.6 l/min STp and the Fischer-Tropsch catalyst (300 g) was the same as used in Example 3.

The catalytic reaction was carried out at a temperature of 343°C, a pressure of 20.4 atmospheres gauge and a space velocity of 8,800 hr$^{-1}$ to a conversion of CO of about 96.8 percent. The effluent had a mol ratio of hydrogen to total hydrocarbons and oxygenated hydrocarbons having three or more carbon atoms of about 16.3.

The hydropyrolysis reaction was carried out at a temperature of 815°C, a pressure of 20.4 atmospheres gauge and a residence time of about 0.5 second. A level of 105 ppm $H_2S$ were added to the feed to the pyrolysis reactor.

The analyses of the catalytic reaction effluent and the hydropyrolysis effluent are set forth in Table V.

TABLE V

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 29.8 | 30.5 | | |
| $H_2$ | 10.7 | 8.7 | | |
| CO | 2.6 | 2.9 | | |
| $CO_2$ | 25.6 | 25.5 | | |
| $C_1{}^a$ | 6.5 | 13.1 | 20.8 | 40.5 |
| $C_2{}^a$ | 4.5 | 16.9 | 14.5 | 52.3 |
| $C_3{}^a$ | 5.7 | 1.2 | 18.2 | 3.8 |
| $C_4{}^a$ | 4.2 | 0.3 | 13.5 | 0.8 |
| $C_5{}^a$ | 3.1 | 0.04 | 9.8 | 0.1 |
| $C_6+{}^a$ | 7.0 | 0.8 | 22.2 | 2.6 |

${}^a$These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

EXAMPLE 6

A further run was carried out in accordance with Example 1 with the mol ratio of hydrogen to carbon monoxide in the feedstock to the catalytic reaction being about 3, except that the $H_2$ rate was 19.9 l/min STP and the CO rate was 6.6 l/min STP and the Fischer-Tropsch catalyst was the same as used in Example 3.

The catalytic reaction was carried out at a temperature of 343°C, a pressure of 20.4 atmospheres gauge and a space velocity of 8,900 $hr^{-1}$ to a conversion of CO of about 98.1 percent. The effluent had a mol ratio of hydrogen to total hydrocarbons and oxygenated hydrocarbons having three or more carbon atoms of about 15.9.

The hydropyrolysis reaction was run at a temperature of 799°C, a pressure of 20.4 atmospheres gauge and a residence time of 0.5 second.

The analyses of the catalytic reaction effluent and the hydropyrolysis effluent are set forth in Table VI.

TABLE VI

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 27.6 | 32.1 | | |
| $H_2$ | 10.2 | 7.8 | | |
| CO | 1.6 | 7.7 | | |
| $CO_2$ | 29.7 | 20.9 | | |
| $C_1{}^a$ | 6.4 | 12.8 | 20.8 | 40.2 |
| $C_2{}^a$ | 4.3 | 14.9 | 13.9 | 46.9 |
| $C_3{}^a$ | 5.2 | 2.8 | 16.8 | 8.7 |
| $C_4{}^a$ | 3.9 | 0.5 | 12.6 | 1.6 |
| $C_5{}^a$ | 2.7 | 0.1 | 8.8 | 0.4 |
| $C_6+{}^a$ | 8.4 | 0.7 | 27.1 | 2.2 |

${}^a$These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

EXAMPLE 7

A further run was carried out in accordance with Example 1 with the mol ratio of hydrogen to carbon monoxide in the feedstock to the catalytic reaction being about 3, except that the $H_2$ rate was 19.9 l/min STP and the CO rate was 6.6 l/min STP and the Fischer-Tropsch catalyst was the same as used in Example 3.

The catalytic reaction was carried out at a temperature of 343°C, a pressure of 20.4 atmospheres gauge and a space velocity of 8,800 $hr^{-1}$ to a conversion of CO of about 96.8 percent. The effluent had a mol ratio of hydrogen to total hydrocarbons and oxygenated hydrocarbons having three or more carbon atoms of about 16.3.

Prior to introducing the effluent to the hydropyrolysis zone, 3.67 ml/min n-hexane (liquid) were preheated and introduced to the effluent thus enriching the $C_3+$ content for pyrolysis. The mol ratio of hydrogen to total hydrocarbons and oxygenated hyrocarbons having 3 or more carbon atoms in the mixture was about 15.0.

The hydropyrolysis reaction was run at a temperature of 846°C, a pressure of 20.4 atmospheres gauge, and a residence time of about 0.5 second. A level of 730 ppm $H_2S$ were added to the feed to the hydropyrolysis reactor.

The analysis of the catalytic reaction effluent and the hydropyrolysis effluent are set forth in Table VII.

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2O$ | 29.8 | 23.0 | | |
| $H_2$ | 10.7 | 2.0 | | |
| CO | 2.6 | 2.6 | | |
| $CO_2$ | 25.6 | 20.1 | | |
| $C_1{}^a$ | 6.5 | 19.5 | 20.8 | 37.4 |
| $C_2{}^a$ | 4.5 | 28.4 | 14.5 | 54.4 |
| $C_3{}^a$ | 5.7 | 2.2 | 18.2 | 4.3 |
| $C_4{}^a$ | 4.2 | 0.6 | 13.5 | 1.2 |
| $C_5{}^a$ | 3.1 | 0.2 | 9.8 | 0.3 |
| $C_6+{}^a$ | 7.0 | 1.3 | 22.2 | 2.4 |

${}^a$These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

EXAMPLE 8

A similar run to that of Example 7 was made except that 3.33 ml/min of kerosene (liquid) were preheated and introduced to the effluent rather than n-hexane. The kerosene had a boiling point range of 190° to 270°C and a specific gravity of 0.82. The mol ratio of hydrogen to total hydrocarbons and oxygenated hydrocarbons having three or more carbon atoms in the mixture was about 15.5.

The hydropyrolysis reaction was conducted as in Example 7 except the temperature was 835°C and only a level of 105 ppm $H_2S$ were added to the feed.

The analysis of the catalytic reaction effluent and the hydropyrolysis effluent are set forth in Table VIII.

| Component | PRODUCT ANALYSIS (WEIGHT PERCENT) | | DISTRIBUTION (WEIGHT PERCENT) | |
|---|---|---|---|---|
| | From Catalytic Reaction | From Hydropyrolysis | From Catalytic Reaction | From Hydropyrolysis |
| $H_2$ | 29.8 | 23.0 | | |
| $H_2O$ | 10.7 | 2.1 | | |
| CO | 2.6 | 2.6 | | |
| $CO_2$ | 25.6 | 20.1 | | |
| $C_1^a$ | 6.5 | 16.8 | 20.8 | 32.1 |
| $C_2^a$ | 4.5 | 21.0 | 14.5 | 40.2 |
| $C_3^a$ | 5.7 | 3.4 | 18.2 | 6.6 |
| $C_4^a$ | 4.2 | 1.1 | 13.5 | 2.1 |
| $C_5^a$ | 3.1 | 0.6 | 9.8 | 1.2 |
| $C_6+^a$ | 7.0 | 9.3 | 22.2 | 17.9[b] |

[a] These figures include both hydrocarbons and oxygenated hydrocarbons in products from the catalytic reaction whereas the figures for hydropyrolysis products represent only hydrocarbons since any original oxygenated hydrocarbons are converted to hydrocarbons in the hydropyrolysis reactor.

[b] This figure reflects the high aromatic content of the kerosene which does not pyrolyze but can be recovered as predominantly benzene, toluene and xylenes.

Thus having described the invention in detail it will be understood by those skilled in the art that certain variations and modifications may be made without departing from the spirit and scope of the invention as described herein or defined in the appended claims.

I claim:

1. A process for producing ethane and/or ethylene comprising
   a. introducing hydrogen and carbon monoxide to a catalytic reaction zone, the mol ratio of hydrogen to carbon monoxide being in the range of about 1/1 to about 5/1;
   b. reacting said hydrogen and carbon monoxide in the catalytic reaction zone to a conversion of at least 50 percent of the carbon monoxide and thereby producing a catalytic reaction zone effluent containing hydrogen, carbon monoxide, water, hydrocarbons, and oxygenated hydrocarbons, said reaction being carried out under conditions of temperatures in the range of about 150°C to 450°C, pressures in the range of atmospheric to about 75 atmospheres and space velocities in the range of 500 to 50,000 V/V/hr STP, in the presence of a Fischer-Tropsch catalyst containing iron, cobalt, nickel or ruthenium;
   c. introducing directly to a hydropyrolysis zone at least a portion of the catalytic reaction zone effluent containing hydrogen, carbon monoxide, carbon dioxide, water, hydrocarbons and oxygenated hydrocarbons, together with any necessary hydrogen required to bring the mol ratio of hydrogen to total hydrocarbons and oxygenated hydrocarbons having at least three carbon atoms to at least 1/1;
   d. hydropyrolyzing said catalytic reaction zone effluent to produce a hydropyrolysis zone effluent, said hydropyrolyzing being carried out under conditions of temperatures in the range of about 600°C to 900°C, pressures of at least 5 atmospheres gauge and residence times in the range of about 0.1 sec to 60 sec;
   e. and recovering $C_2$ hydrocarbons from said hydropyrolysis zone effluent.

2. A process according to claim 1 wherein the hydrogen and carbon monoxide are introduced to the catalytic reaction zone in the form of a desulfurized effluent from gasification of coal with steam and oxygen.

3. A process according to claim 1 wherein the catalytic reaction is carried out under conditions of temperatures in the range of 200°C to 400°C, pressures in the range of 5 to 75 atmospheres gauge and space velocities in the range of 3,000 to 10,000 V/V/hr STP.

4. A process according to claim 3 wherein the temperatures are in the range of 250°C to 350°C and the pressures are in the range of 10 to 30 atmospheres gauge in the catalytic reaction.

5. A process according to claim 1 wherein the hydrogen/carbon monoxide mol ratio being introduced to the catalytic reaction is in the range of 2/1 to 4/1.

6. A process according to claim 3 wherein the hydropyrolysis is carried out under conditions of temperatures in the range of 700°C to 850°C, pressures in the range of 5 to 100 atmospheres gauge and residence times of 0.5 to 20 seconds.

7. A process according to claim 6 wherein the hydropyrolysis pressure is in the range of 15 to 30 atmospheres gauge.

8. A process according to claim 1 wherein additional hydrocarbons are combined with the catalytic reaction zone effluent prior to introduction to the hydropyrolysis zone.

9. A process according to claim 1 wherein the catalytic reaction zone effluent is divided into two portions, each portion containing hydrogen, carbon monoxide, carbon dioxide, water, hydrocarbons, and oxygenated hydrocarbons; separating the hydrocarbons and oxygenated hydrocarbons from one portion; recombining the separated hydrocarbons and oxygenated hydrocarbons with the other portion of the effluent; and introducing the thus combined materials to the hydropyrolysis zone.

10. A process according to claim 1 wherein hydrogen is separated from the hydropyrolysis zone effluent and recycled to the catalytic reaction zone and/or the hydropyrolysis zone.

11. A process according to claim 1 wherein the hydrocarbons having three or more carbon atoms are separated from the hydropyrolysis zone effluent and recycled to the hydropyrolysis zone.

* * * * *